United States Patent [19]

Poplawski

[11] Patent Number: 4,964,628

[45] Date of Patent: Oct. 23, 1990

[54] HIP-RECIPROCATING APPARATUS

[75] Inventor: Christopher Poplawski, Redwood City, Calif.

[73] Assignee: Center for Orthotics Design, Inc., Redwood City, Calif.

[21] Appl. No.: 375,210

[22] Filed: Jun. 30, 1989

[51] Int. Cl.$^5$ .............................................. A63B 23/04
[52] U.S. Cl. ..................................................... 272/70
[58] Field of Search ......................... 272/70, 70.3, 70.4; 128/25 R, 25 B; 623/27, 30, 32

[56] References Cited

U.S. PATENT DOCUMENTS

| 2,010,482 | 8/1935 | Cobb | 128/25 R |
| 2,210,269 | 8/1940 | Taylor | 272/70.3 X |
| 4,697,808 | 10/1987 | Larson et al. | 272/70 |

FOREIGN PATENT DOCUMENTS

| 975012 | 11/1982 | U.S.S.R. | 272/70 |
| 14477 | of 1904 | United Kingdom | 272/70 |

OTHER PUBLICATIONS

W. Motloch, "A New Item for the Spina Bifida Program", Inter-Clinic Information Bulletin, vol. IX, No. 10, pp. 10–13, Jul. 1970.
W. Motloch, Instruction Manual, "The Reciprocating Gait Brace (Gear Type)", Prosthetic Services, Department of National Health, and Welfare, c/o Sunnybrook Hospital, Toronto, Canada, approx. 1971.
W. Motloch, "Orthotic Philosophies of Treatment", editorial in *Clinical Prosphetics and Orthotics Journal*, vol. 8, No. 4, Fall 1984, pp. 9–11.
"Reciprocating Gait Brace Cord and Pulley Type", Annual Report, Ontario Crippled Children's Center, Ontario, Canada, approx. 1968, pp. 8–243 and 8–244.
S. Parker, "Amazing Invention Allows Paraplegic to Walk", Chattanooga News–Free Press, p. D–8, Sep. 28, 1980.
Durr–Fillauer Medical, Inc., Orthopedic Division, "LSU Reciprocating Gait Orthosis Cable Assemblies and Attachment Pieces", 4 page Catalog.

*Primary Examiner*—Richard J. Apley
*Assistant Examiner*—H. Flaxman
*Attorney, Agent, or Firm*—Edward B. Anderson

[57] ABSTRACT

A hip reciprocating apparatus of a reciprocating gait brace provides for transfer of forces from movement of one leg to a reverse movement of the other leg of a user. A C-shaped pivot member pivots about a horizontal axis and is mounted at the back of the pelvic band of a gait brace. The pivot member ends are adjacent hip joints which couple the pelvic band to a leg or lower hip joint member. A length-adjustable tie rod couples the pivot member ends to posteriorly extending protrusions of the associated leg member. The pivot point of the pivot member may be equally or unequally spaced relative to the pivot member ends. The leg member protrusions may be of different lengths. A spring may be used to store energy during pivoting of the pivot member in one direction and release of the energy during pivoting in the other direction. An external power source may apply energy to movement of the pivot member in both directions.

16 Claims, 8 Drawing Sheets

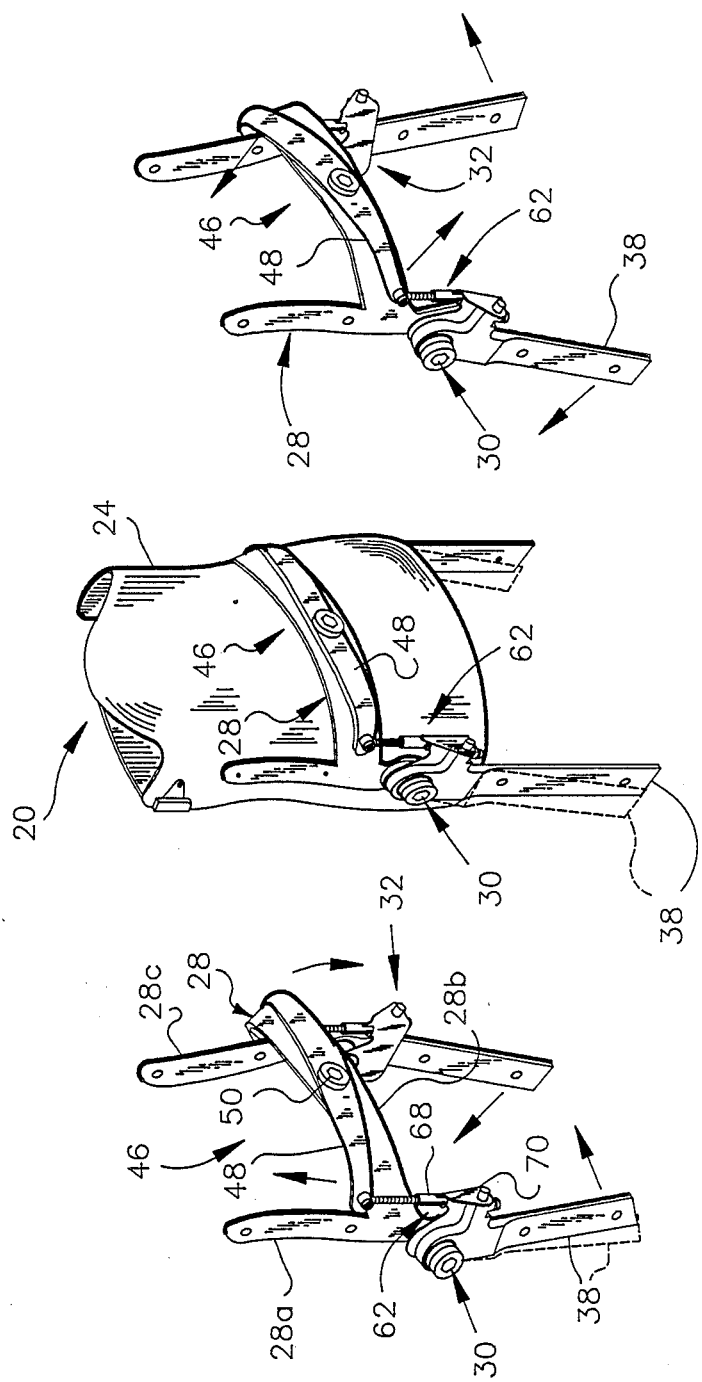

HIP-RECIPROCATING APPARATUS

FIELD OF THE INVENTION

This invention relates to orthopedic appliances for facilitating walking of a physically impaired individual, and particularly to apparatus supported exteriorly to the body for coordinating the flexion and extension of the two legs during walking and for standing balance.

BACKGROUND AND SUMMARY OF THE INVENTION

Many people are sufficiently physically impaired that they are unable to use their legs or have very limited or unbalanced use of their legs, and are thus conventionally restricted to self-powered mobility in the form of a wheel chair or stiff leg braces used with a walking frame which nearly surrounds the user.

These conventional limitations of mobility have been overcome to a large degree by a cable-based orthopedic appliance often referred to as a reciprocating gait orthosis or brace, such as the device sold under the proprietary name of "LSU Reciprocating Gait Orthosis" by Durr-Fillauer Medical, Inc. of Chattanooga, Tenn. This device uses right and left hip joint assemblies. Each hip joint assembly includes a lower hip joint bar which rotates relative to an upper hip joint bar. The upper bar is fixed in position relative to the side of the torso of the user. The lower bar is fixed in position relative to the outer side of the upper leg of the user, forming a hip joint where the two bars are pivotally attached. Hip joint assembly on each side, in effect, has protrusions which extend anteriorly and posteriorly of the pivot connection. A cable connects the two anteriorly extending protrusions and a second cable connects the two posteriorly extending protrusions. These cables extend slidably in sheathes that are fixed in position to the upper bars.

One way to change the relative rotational positions of the upper and lower bars is by replacing the cables with cables of different lengths. This is desirable where the individual is not able to stand fully upright due to the shortening of muscles in the front of the hip.

Further, the anteriorly extending protrusions on the lower bars cause bulges in the clothing of the user and prevent the natural spreading of the hips when the user assumes a sitting position. The cable travelling through the sheath provides resistance to leg movement in the form of friction. This friction causes heating and wearing of the sheath wastes energy and tires the patient. The range of hip motion may be limited by an insufficient length of bare cable between the sheath end and the cable attachment at the hip joint assembly. The cable linkage typically has some free play which allows the lower hip joint bars to move a little without transferring force between them.

It is also desirable to have a hip reciprocating apparatus which takes up less space, operates simply, is less expensive to make, and is lighter in weight.

The present invention provides a hip reciprocating apparatus which overcomes these disadvantages of the prior art. In particular, it provides such an apparatus which minimizes friction, improves cosmesis, and is simple in design, structure and operation.

Generally, the present invention provides an apparatus positionable adjacent the hips of a human body for facilitating walking. Included is a base member, also referred to as a reciprocating gait brace, positionable adjacent the hips of a human body and extending from one hip to the other hip when positioned for use. A pivot member has an end extending adjacent each hip and is attached to the base member for pivoting relative to the base member in a manner whereby the pivot member ends move vertically in opposite directions with pivoting of the pivot member. A leg member is attached to the base member adjacent each hip and extends along the human leg for pivoting relative to the base member about an axis extending laterally of the base member. Finally, a linkage couples each pivot member end with the associated leg member for pivoting the two leg members when the pivot member pivots relative to the base member.

In a preferred embodiment of the present invention, the base member, positionable adjacent the hips of a human body, has a back extending from one hip, behind the torso of the body, to the other hip when positioned for use. The pivot member is elongate in a C-shape, extends across the back of the base member between ends that are adjacent each hip, and is attached at a central location to back of the base member. The pivot member pivots about a generally horizontal axis relative to the base member in a manner whereby the pivot member ends move vertically in opposite directions with pivoting of the pivot member.

Each leg member pivots relative to the base member about an axis extending laterally of the base member. The linkage is adjustable in length and is attached to the leg member posteriorly of the pivot axis between the leg member and base member.

It can be seen that such a device provides many advantages over the prior art. The pivot arm transfers force from one leg to the other by a simple mechanically direct means which fits into the small of the user's back, has only the minimal friction of pivot joint, provides an extended range of hip motion, and has reduced manufacturing costs and other advantages.

These and other features and advantages of the present invention will be apparent from the following detailed description and the accompanying drawings.

BRIEF DESCRIPTION OF THE DRAWINGS

FIG. 2 is a view similar to FIG. 1 showing a partial view of the apparatus with the right leg member in an flexed position.

FIG. 3 is a view similar to FIG. 2 showing the leg members in an intermediate or neutral position.

FIG. 4 is a view similar to FIG. 2 showing the right leg member in an extended position.

DETAILED DESCRIPTION OF THE PREFERRED EMBODIMENT

Figure 1:
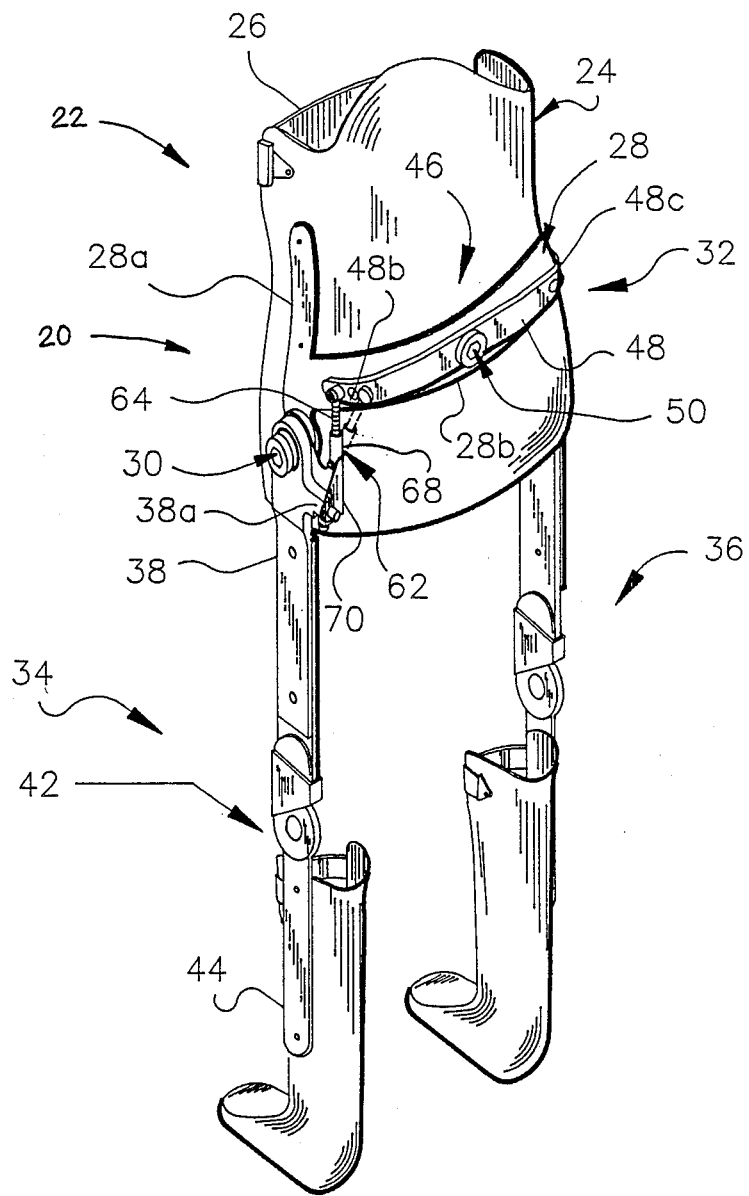
FIG. 1 is a left-side, rear perspective view of a preferred embodiment of a hip reciprocating apparatus made according to the present invention.

Referring initially to FIGS. 1-7, a first preferred embodiment of a hip reciprocating apparatus 20 made according to the present invention is shown. FIG. 1 shows apparatus 20 as part of a complete reciprocating gait brace 22. Brace 22 includes a torso vest 24 made conventionally of a rigid padded structure. Vest 24 is positionable on the rear torso of a human body by straps, such as straps 26 extending across the front of the torso. A rigid pelvic strap or band 28 extends from a left upper hip bar portion 28a, adjacent to the lower back of a user along an intermediate portion 28b, to a right upper hip bar portion 28c. Portion 28c is not shown in FIG. 1, but is shown in FIGS. 2 and 4. Vest 24 and pelvic band 28 are also referred Attached to the lower sections of the left and right upper hip bar portions are left and right hip joints 30 and 32. These hip joints are similarly constructed, so that only left hip joint 30 will be described, with the understanding that an equivalent description also applies to the right hip joint.

The hip joints provide for pivoting of left and right leg assemblies 34 and 36. Left leg assembly 34 includes a lower hip joint bar or leg member 38 which pivots at left hip joint 30 about a generally horizontal axis 40 extending laterally of vest 24. This provides an external hip joint which preferably is positioned in line with the natural hip joint of a user wearing gait brace 22.

The leg assemblies also preferably include a knee joint 42 and lower-leg-supporting boot 44 that securely hold the leg in position relative to leg member 38. As the leg assemblies, other than the leg members, do not form part of the present invention, and are of conventional structure, they are not described further.

The structure that has been described to this point is conventional. The essence of the present invention is therefore embodied in a pivot arm assembly 46 attached to pelvic band 28. Assembly 46 includes a preferably C-shaped pivot member or bar 48. Member 48 has an arc shape when viewed from above so that it generally conforms to the contour of the back of vest 24 and pelvic band 28.

Figure 5:
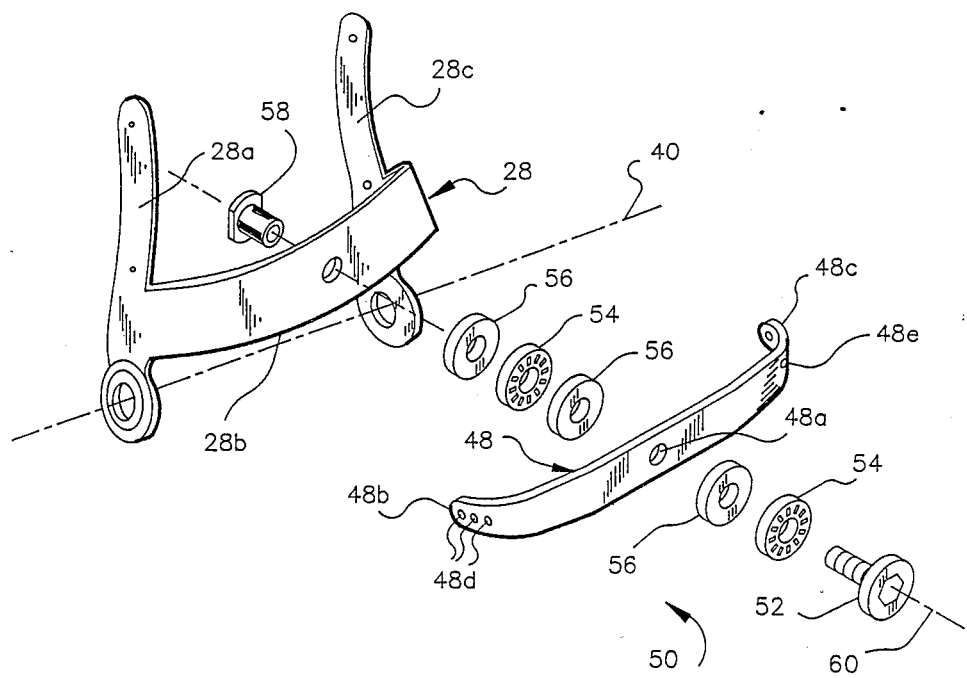
FIG. 5 is an exploded perspective view of the pivot joint of the C-shaped pivot member or bar of the preferred embodiment.
Figure 6:
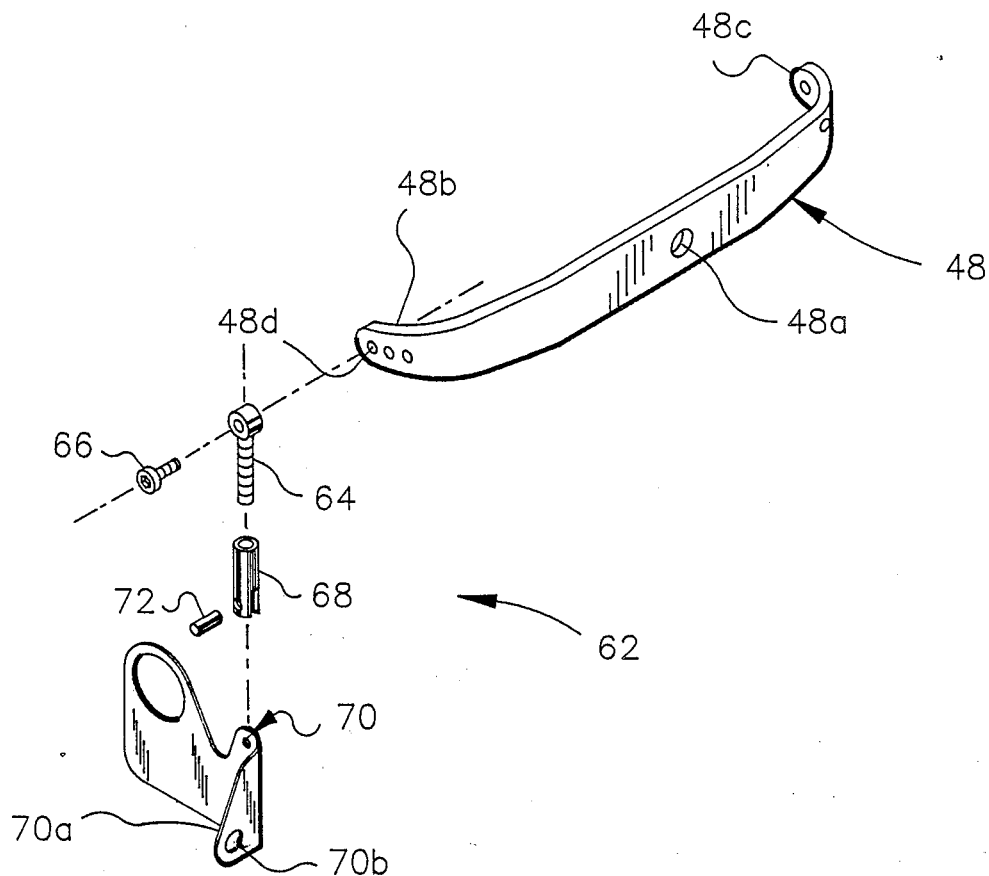
FIG. 6 is an exploded perspective view of the linkage assembly of the preferred embodiment.

Member 48 is pivotally attached to band 28 by a pivot joint 50. As shown in FIG. 5, pivot joint 50 includes a joint screw 52, thrust bearings 54, thrust washers or races 56, and joint nut 58 which sandwich member 48 to band 28 for pivoting about a pivot axis 60. A hole 48a through which the joint screw extends is preferably located equidistant from left hip joint 30 and right hip joint 32. As will be seen, this provides for equal movement of member ends 48b and 48c.

At each end of pivot member 48 is a tie rod assembly 62, also referred to as linkage means, that couples the pivot member end to an associated lower hip bar or leg member. Tie rod assembly 62, as shown in further detail in FIG. 6, includes a threaded shaft or rod 64 pivotally coupled to pivot member end 48b (and 48c) by a pivot screw 66 which screws into a threaded hole 48d and allows rod 64 to pivot relative to member 48.

The threaded end of rod 64 is matingly received in a threaded sleeve or yoke 68. The lower end of yoke 68 includes an opening that receives an edge of a coupling plate 70. The yoke and coupling plate are pivotally attached by a pivot pin 72.

Tie rod assembly 62 is adjustable in length like a turn buckle. By varying the distance between the pivot arm end and the coupling plate, the torso alignment of an upright person is adjusted. The torso alignment can thus be fine tuned to provide the front-to-back alignment of the torso that provides the best alignment and stability.

In this preferred embodiment, it will be noted that the pivot screw must be removed, or the pivot pin removed, in order to adjust the length of assembly 62. Yoke 68 could be replaced by a smooth yoke sleeve with a captured nut screwed onto screw 66 and having edges exposed. The length could then be adjusted by the user by simply turning the nut within the sleeve, if it is desired to give the user this capability.

Figure 7:
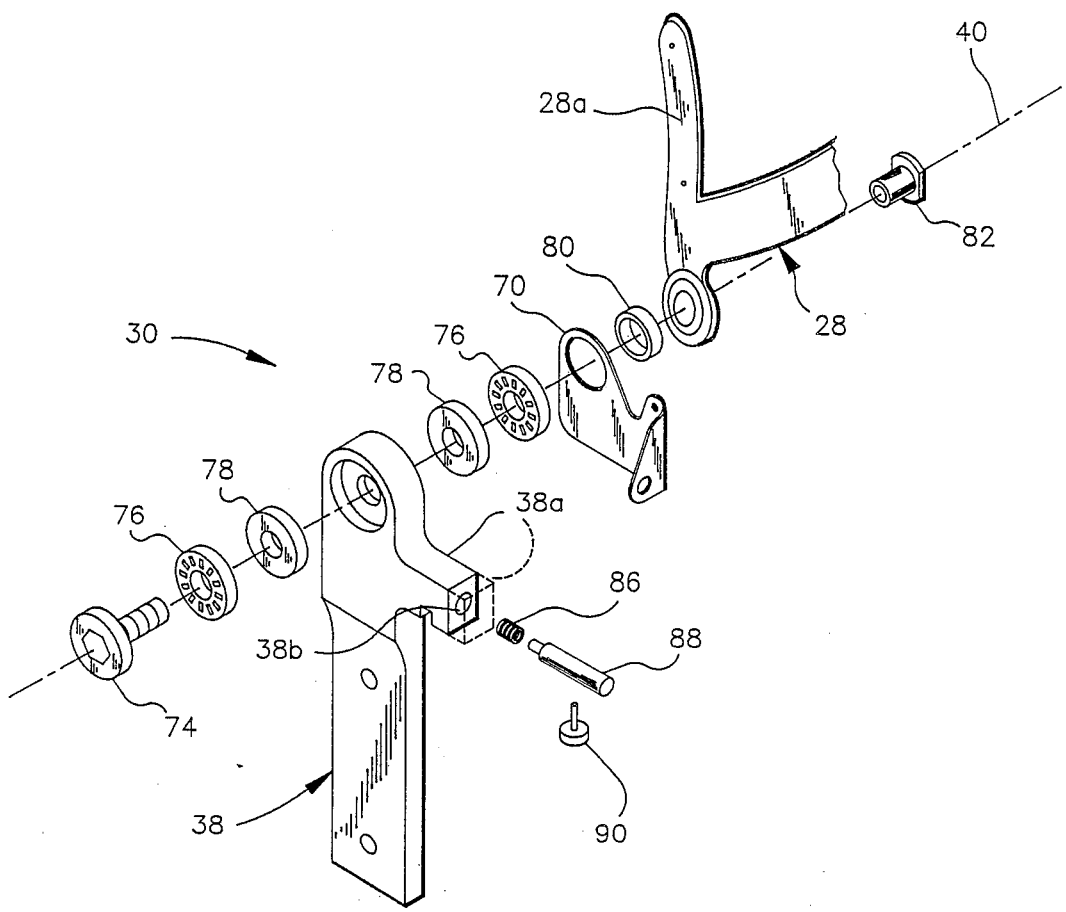
FIG. 7 is an exploded perspective view of the left hip joint assembly of the preferred embodiment.

Coupling plate 70 also forms part of the hip joints, such as left hip joint 30 shown in expanded view in FIG. 7. Pelvic band left side 28a, coupling plate 70, and left leg member 38 are sandwiched together in a conventional fashion with a joint screw 74, thrust bearings 76, thrust races 78, a spacer 80, and a joint nut 82. This joint provides for pivoting about a generally horizontal axis 84 extending laterally of, or into the side of, vest 24, as shown.

Leg member 38 includes a posterior extension 38a which has a bore 38b extending into it. This bore receives a latch spring 86 and a latch plunger 88, which serve to lock the hip joint when the bore is aligned with a corresponding bore in the pelvic band portion of the hip joint. The plunger is held in place by a latch knob 90 which passes through an unseen threaded bore to seat against the plunger. Coupling plate 70 includes a folded section 70a that is aligned with the end face of extension 38a, and has an opening 70b. Latch plunger 88 extends through opening 70b when the hip joint is assembled for use, thereby holding the coupling plate in a fixed position relative to the leg member.

Extension 38a may be extended further than is shown in solid lines. Such an extension is shown in dashed lines at 38c. Coupling plate 70 would also be extended to conform to this extension With the extension longer, the tie rod assembly is coupled to the leg member at a position spaced further from hip joint axis 40. By making the extension on each side of a different length, the arcs that the corresponding leg members swing are of corresponding different amounts. The leg member having the longer extension swings through a shorter arc. This feature is useful for a person having different ranges of movement of the two legs.

Also, by making them both longer or shorter, different uniform ranges of movement and different leverage is provided for using the hip reciprocating apparatus. The longer the extension, the shorter the arc or leg ember movement for a given pivot of the pivot member, but the greater the leverage in transferring forces from one leg to the other.

Referring now to FIGS. 1-4, the operation of apparatus 20 is illustrated. In FIG. 1, gait brace 22, including apparatus 20, is shown in the position it would have when worn by a user in a vertical, standing position. When the user flexes her or his right leg forward, pivot member 48 rotates in a clockwise direction, as viewed from the rear. This is the position shown in FIG. 2. The raising of end 48b results in left leg member 38 pivoting backwards, as occurs during normal walking.

The user's weight is then shifted to the right leg, and the left leg is moved forward. This causes the user's body to move forward, to accommodate the relative rearward positioning of the right leg member. An intermediate position is reached, as shown in FIG. 3. As the left leg continues forward, a position is reached with the left leg member flexed forward and the right leg member extended rearward, as shown in FIG. 4. By repeating this procedure of alternately flexes each leg forward, both legs are caused to move in a relatively conventional manner.

As was indicated previously, each tie rod assembly is adjustable in length. FIG. 3 illustrates the position of leg member 38, in dashed lines, when the left tie rod assembly is extended relative to the right tie rod assembly. This results in the left leg member not extending back as far as the right leg member will. It also results in the left leg member flexes further forward than the corresponding movement of the right leg member. This feature can be used to accommodate unusual differences in leg mobility.

Adjustment of the length of the tie rod assembly changes the angular or pivot position of the leg member relative to the associated side of pelvic band 28. Thus, by adjusting both sides, the alignment of the leg member relative to the pelvic band is altered, as shown in dashed lines in FIG. 3. This corresponds, as discussed previously with reference to FIG. 6, to an ability to accommodate the torso and leg alignment capabilities of each user.

Figure 8:
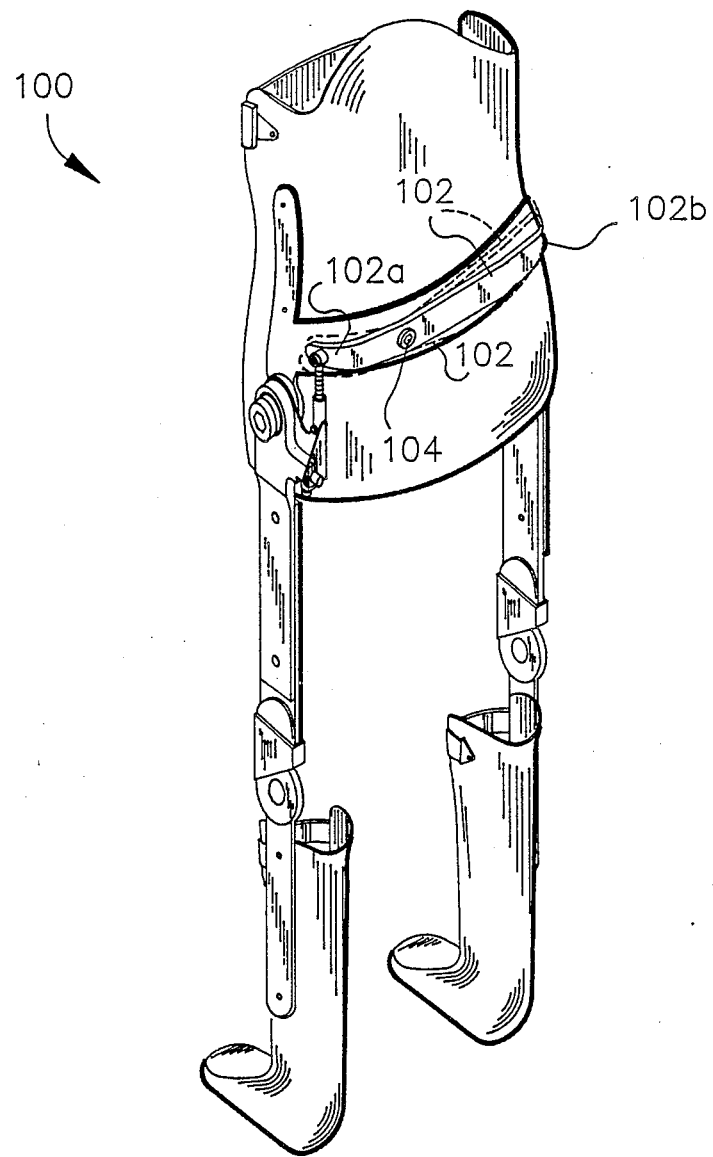
FIG. 8 is a view similar to FIG. 1 showing an second embodiment of the invention.

FIG. 8 shows a second preferred embodiment of a hip reciprocating apparatus 100. Apparatus 100 is structured the same as apparatus 20 except that a pivot member 102 is pivotally attached at a pivot joint 104 at a position which is closer to pivot member left end 102a than to the right end 102b. This provides for uneven transfer of forces between the user's legs. In the embodiment shown, the right leg will swing through a much greater range of movement than the left leg, as is illustrated by the movement of pivot member 102 shown in dashed lines. This embodiment is useful when one leg has hip joint stiffness or weakness.

The present invention also provides means for applying energy to the pivot member. Two embodiments providing this feature of the invention are shown in FIGS. 9 and 10.

Figure 9:
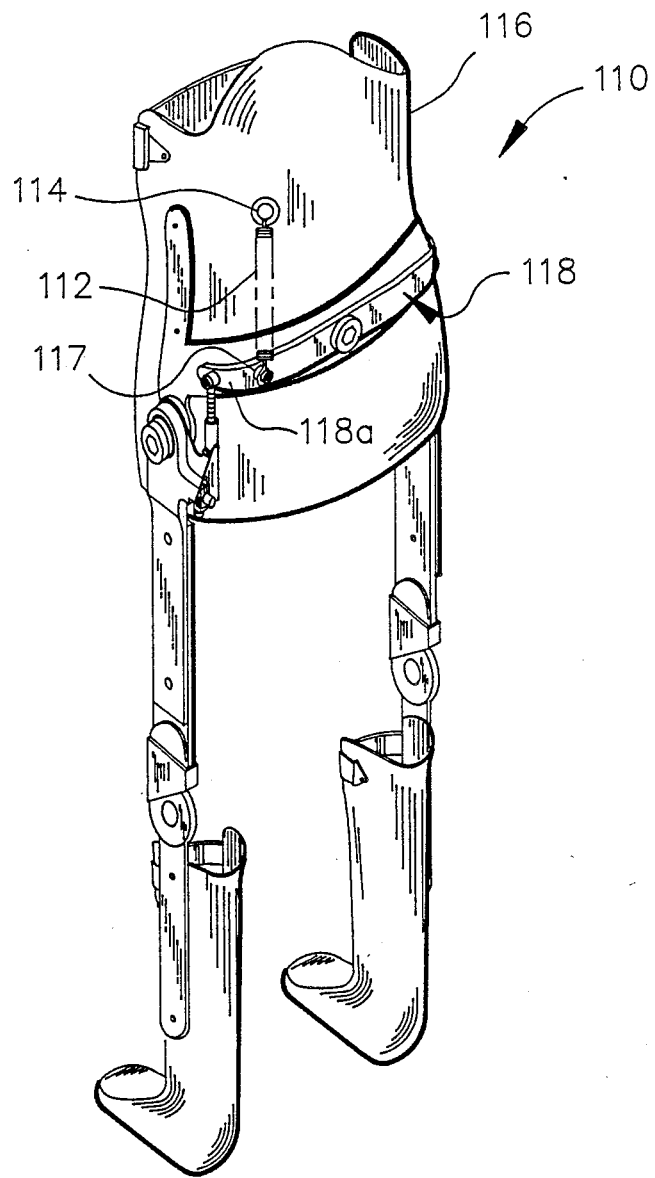
FIG. 9 is a view similar to FIG. 1 showing a third embodiment of the invention.
Figure 10:
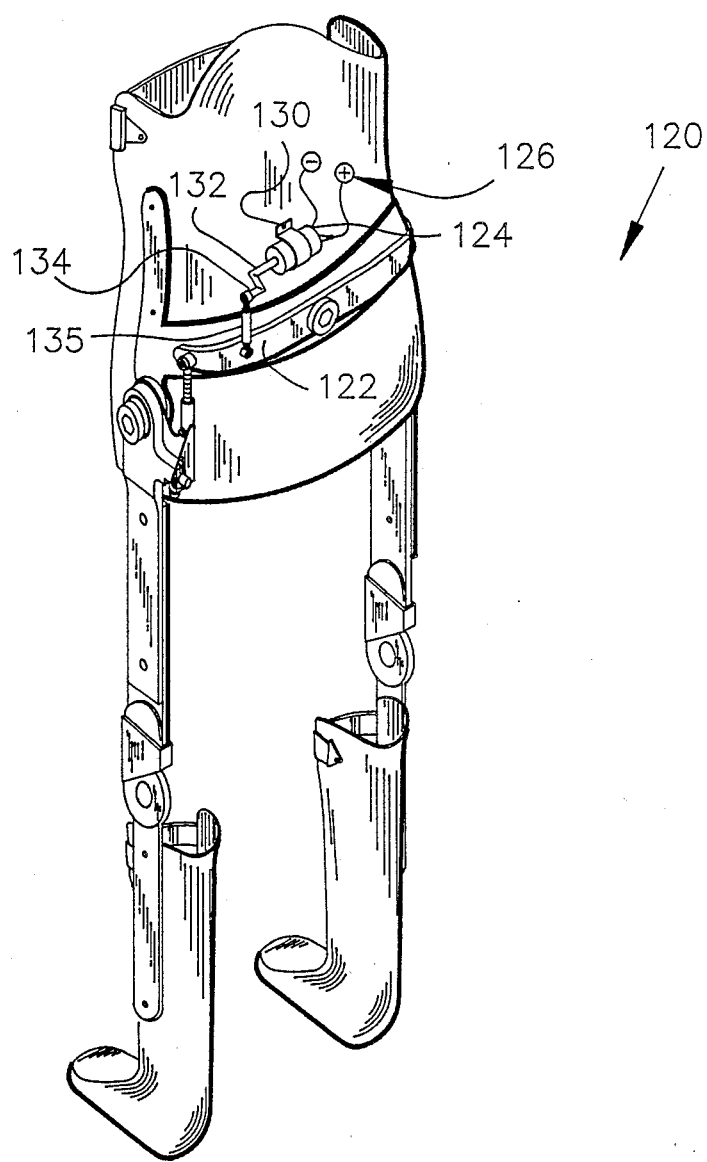
FIG. 10 is also a view similar to FIG. 1 showing a fourth embodiment of the invention.

In FIG. 9, a hip reciprocating apparatus 110 is structured substantially the same as apparatus 20. The only difference in this embodiment is that a spring 112 extends between a mounting 114 fixedly attached to a torso vest 116 and a mounting 114 fixedly attached to the pivot member 118 or 102 adjacent right or left end 118, as shown.

Spring 112 may be either a compression spring or a tension spring. In either form, during one direction of pivoting of the pivot member, the spring will act to resist the pivoting, thereby storing energy. As the pivot member pivots in the reverse direction, the stored spring energy acts as a force applied to the pivot member, facilitating motion in that direction. Preferably, the spring relaxed-state position will be set at a full extension position of one of the leg members.

This embodiment is useful where one leg is stronger than the other leg. The stronger leg movement is used to store energy in the spring, which then acts to move the weaker leg forward during the next step. It will be noted that other energy storage means, such as elastic bands, leaf springs and air compression, may also be used.

The other energy-applying embodiment is illustrated in FIG. 10. In this embodiment, the hip reciprocating apparatus 120 includes means for applying energy to both directions of movement of the pivot member 122. The driving means in this embodiment is preferably an external power source, such as a motor 124 coupled to a power supply shown generally at 126, such as a battery.

Motor 124 is held in position on the torso vest 128 by a suitable bracket 130. A shaft 132 extending from the motor has an eccentrically positioned cam arm 134 which rotates about the shaft spin axis. A tie rod 135 couples the cam arm 134 to pivot member 122 at a position spaced from the pivot joint, as shown. As cam arm 134 moves, pivot member 122 is pivoted reciprocally about the pivot member pivot axis. The motor may be controlled by a manually operable or gravity-sensitive switch, a rheostat, or other suitable means. Other power sources may also be used, such as hydraulics, compressed air, or other suitable electrically driven devices. The power source could also be applied to a leg member.

It will be understood that the foregoing description is directed to preferred embodiments of various features of the present invention. Variations in design and structure may be made without parting from the spirit and scope of the invention as described in the claims. For instance, features described with reference to one side may be applied equally as well to the other side of the apparatus. Further, specific dimensions and relative relationships may be varied, such as the specific position of an off-center pivot position as in the embodiment of FIG. 8.

I claim:

1. An apparatus positionable adjacent to the hips of a human body for facilitating walking and standing balanced comprising:
   a base member including a hip portion positionable adjacent to each hip of a human body, wherein the base member extends from one hip to the base member extends from one hip to the other hip when positioned for use;
   a pivot member pivotally mounted on the base member, the pivot member including an opposing end extending adjacent to each base member hip portion when positioned for use, whereby the pivot member ends move in opposite directions with pivoting of the pivot member;
   a leg member pivotally attached to each hip portion of the base member and extending along the human leg, when positioned for use, for pivoting relative to the base member about an axis extending laterally of the base member; and
   linkage means coupling each pivot member end with the associated leg member for coordinating the pivoting of the two leg members when the pivot member pivots relative to the base member.

2. An apparatus according to claim 1 wherein the pivot member pivots about an axis disposed centrally between the pivot member ends.

3. An apparatus according to claim 1 wherein the pivot member pivots about an axis disposed closer to one pivot member end than to the other pivot member end.

4. An apparatus according to claim 3 wherein each linkage means attaches to the associated leg member a predetermined distance from the leg member pivot axis, and the predetermined distance is different for each leg member.

5. An apparatus according to claim 4 wherein the predetermined distance is shorter for the leg member closer to the pivot-member pivot axis.

6. An apparatus according to claim 1 wherein each linkage means attaches to the associated leg member a predetermined distance from the leg member pivot axis, and the predetermined distance is different for each leg member 7. An apparatus according to claim 1 further comprising means for applying energy to the pivot member.

8. An apparatus according to claim 7 wherein the energy-applying means stores energy during pivoting of the pivot member in one direction and applies the stored energy to the pivot member during pivoting of the pivot member in the other direction.

9. An apparatus according to claim 8 wherein the energy-applying means comprises a spring attached at one end to the pivot member at a position spaced from the pivot member pivot axis, and attached at the other end to the base member.

10. An apparatus according to claim 7 wherein the energy-applying means applies energy to both directions of pivoting of the pivot member.

11. An apparatus according to claim 10 wherein the energy-applying means comprises a motor having a shaft and means for converting rotational motion of the motor shaft into reciprocating motion of the pivot member.

12. An apparatus according to claim 1 further comprising means for varying the rotational position of a leg member about the pivot axis of the same leg member for a given position of the pivot member about the pivot-member pivot axis.

13. An apparatus according to claim 12 wherein the rotational-position varying is formed in the linkage means for varying the length of the linkage means between the associated pivot member end and leg member.

14. An apparatus according to claim 13 wherein the rotational-position varying means comprises a matingly threaded shaft and sleeve assembly.

15. An apparatus according to claim 1 wherein the linkage means is attached to the leg member posteriorly of the pivot axis between the base member and the leg member.

16. An apparatus positionable adjacent to the hips of a human body for facilitating walking and standing balanced comprising:

a base member including a hip portion positionable adjacent to each hip of a human body and having a back extending between the hip portions from one hip, behind the torso of the body, to the other hip when positioned for use;

an elongate pivot member pivotally mounted at a central location to the back of the base member for pivoting about a generally horizontal axis when positioned for use, the pivot member including an opposing end extending adjacent to each base member hip portion when positioned for use, the pivot member extending across the back of the base member between the opposing ends, whereby the pivot member ends move vertically in opposite directions with pivoting of the pivot member;

a leg member pivotally attached to the base member adjacent to each hip portion and extending along the human leg, when positioned for use, for pivoting relative to the base member about an an axis extending laterally of the base member; and linkage means coupling each pivot member end with the associated leg member for coordinating the pivoting of the two leg members when the pivot member pivots relative to the base member, the linkage means being adjustable in length and being attached to the leg member posteriorly of the pivot axis between the leg member and base member.

* * * * *